US012642509B2

(12) United States Patent
Olivier et al.

(10) Patent No.: US 12,642,509 B2
(45) Date of Patent: Jun. 2, 2026

(54) CIRCULATORY SYSTEM ASSESSMENT

(71) Applicant: KONINKLIJKE PHILIPS N.V., Eindhoven (NL)

(72) Inventors: Antoine Olivier, Suresnes (FR); David Prabhu, Cambridge, MA (US); Patrick Gabriels Rafter, Windham, NH (US); Oudom Somphone, Paris (FR); Caroline Denise Francoise Raynaud, Suresnes (FR); Alexandra Goncalves, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 44 days.

(21) Appl. No.: 18/288,238

(22) PCT Filed: Apr. 15, 2022

(86) PCT No.: PCT/EP2022/060161
§ 371 (c)(1),
(2) Date: Oct. 25, 2023

(87) PCT Pub. No.: WO2022/228919
PCT Pub. Date: Nov. 3, 2022

(65) Prior Publication Data
US 2024/0366188 A1     Nov. 7, 2024

(30) Foreign Application Priority Data
Apr. 29, 2021     (EP) .................................... 21290024

(51) Int. Cl.
*A61B 8/00*        (2006.01)
*A61B 8/08*        (2006.01)
(Continued)

(52) U.S. Cl.
CPC .......... *A61B 8/5223* (2013.01); *A61B 8/0883* (2013.01); *A61B 8/463* (2013.01);
(Continued)

(58) Field of Classification Search
CPC ..... A61B 8/5223; A61B 8/0883; A61B 8/463; A61B 8/469; A61B 8/483; G16H 50/20;
(Continued)

(56) References Cited

U.S. PATENT DOCUMENTS

2013/0155064 A1     6/2013     Grbic et al.
2016/0303804 A1*    10/2016    Grbic ...................... G06T 19/00
(Continued)

OTHER PUBLICATIONS

International Search Report and Written Opinion for PCT/EP2022/060161; Mailing date: Jul. 22, 2022, 17 pages.
(Continued)

*Primary Examiner* — Bo Joseph Peng

(57)                    ABSTRACT
Methods and systems are provided for assessing an area of interest in the circulatory system of a subject. The method comprises: obtaining (210) a temporal sequence of ultrasound image frames of the area of interest; obtaining (220, 320) one or more trained models; inputting (250, 350) the temporal sequence of ultrasound image frames into the one or more trained models; and analysing (260, 360) the temporal sequence of ultrasound image frames, using the one or more trained models, to produce output data characterising a condition of the area of interest, wherein the output data characterises an extent of atherosclerosis or calcification of the area of interest, and wherein the area of interest is the aortic valve. An associated training method for training the one or more models is also provided.

9 Claims, 10 Drawing Sheets

(51) Int. Cl.
    *G16H 50/20*      (2018.01)
    *G16H 50/30*      (2018.01)

(52) U.S. Cl.
    CPC .............. *A61B 8/469* (2013.01); *A61B 8/483*
            (2013.01); *G16H 50/20* (2018.01); *G16H*
                                       *50/30* (2018.01)

(58) Field of Classification Search
    CPC ........ G16H 50/30; G16H 30/40; G06N 3/044;
                           G06N 3/045; G06N 3/084
    See application file for complete search history.

(56)                 References Cited

U.S. PATENT DOCUMENTS

| | | | |
|---|---|---|---|
| 2017/0150928 A1* | 6/2017 | del Alamo de Pedro ................... A61B 5/02028 | |
| 2018/0333104 A1 | 11/2018 | Sitek | |
| 2019/0125295 A1* | 5/2019 | Tek ........................ G16H 40/63 | |
| 2019/0130578 A1* | 5/2019 | Gulsun ................... G06N 3/045 | |
| 2020/0185084 A1 | 6/2020 | Syeda-Mahmood et al. | |

OTHER PUBLICATIONS

Pawade, T. et al., "Calcification in Aortic Stenosis: The Skeleton Key", Journal of the American College of Cardiology, 2015, vol. 66, Issue 5, pp. 561-577.

Shimizu, K. et al., "Usefulness of routine aortic valve calcium score measurement for risk stratification of aortic stenosis and coronary artery disease in patients scheduled cardiac multislice computed tomography", IJC Heart & Vasculature, 2015, vol. 9, pp. 95-99.

Messika-Zeitoun, D. et al., "Evaluation and clinical implications of aortic valve calcification measured by electron-beam computed tomography", Circulation, 2004, vol. 110, No. 3, pp. 356-362.

Rajamannan, N., "Is it time for medical therapy for aortic valve disease?", Expert Rev. Cardiovasc. Ther, 2004, vol. 2, Issue 6, pp. 845-854.

Baumgartner, H. et al., "Recommendations on the Echocardiographic Assessment of Aortic Valve Stenosis: A Focused Update from the European Association of Cardiovascular Imaging and the American Society of Echocardiography", J Am Soc Echocardiogr, 2017, vol. 30, N. 4, pp. 372-392.

Durko, A. et al., "Annual number of candidates for transcatheter aortic valve implantation per country: current estimates and future projections", European Heart Journal, 2018, vol. 39, Issue 28, pp. 2635-2642.

Wang, Z. et al., "Prediction of paravalvular leak post transcatheter aortic valve replacement using a convolutional neural network", IEEE 15th International Symposium on Biomedical Imaging (ISBI 2018), 2018, pp. 1088-1091.

Pollari, F. et al., "Machine Learning for Making Aortic Valve Interventions Complementary and Not Competitive", J Am Coll Cardiol Intv., 2019, vol. 12 , Issue 20, p. 2112.

Simard, L. et al., "Sex-Related Discordance Between Aortic Valve Calcification and Hemodynamic Severity of Aortic Stenosis: Is Valvular Fibrosis the Explanation?", Circ Res., 2017, vol. 120, Issue 4, pp. 681-691.

Clavel, M-A. et al., "The Complex Nature of Discordant Severe Calcified Aortic Valve Disease Grading", Journal of the American College of Cardiology, 2013, vol. 62, Issue 24, pp. 2329-2338.

\* cited by examiner

200

500

600

700

Obtain training data from a training subject

610

Obtain temporal training sequence(s)

Obtain ground truth data          620

Align temporal training sequence(s)          730

Train the model          760

Input aligned temporal training sequence(s) and ground truth data into model

CIRCULATORY SYSTEM ASSESSMENT

CROSS-REFERENCE TO PRIOR APPLICATIONS

This application is the U.S. National Phase application under 35 U.S.C. § 371 of International Application No. PCT/EP2022/060161, filed on Apr. 15, 2022, which claims the benefit of European Patent Application No. 21290024.5, filed on Apr. 29, 2021. These applications are hereby incorporated by reference herein.

FIELD OF THE INVENTION

This invention relates to the use of ultrasound image frames to assess a condition of a portion of the circulatory system of a subject. In particular, it may be used for assessing the condition of a portion of the subject's cardiovascular system—such as their aortic valve.

BACKGROUND OF THE INVENTION

Basic methods of grading the severity of circulatory system conditions are well-known. Traditionally, risk assessments are carried out by a clinician to determine the health of a subject, and the likelihood of the subject being at risk of circulatory (for example, cardiovascular) diseases. These risk assessments analyse risk factors such as gender, age, smoking status, cholesterol levels, diabetes status, and family history.

Additionally, imaging of circulatory systems of subjects takes place, in order to determine further information about the condition of a portion of a subject's circulatory system. For example, subjects may receive echocardiograms, from which cardiovascular conditions can be identified and graded, using data such as dimensions of portions of the cardiovascular system and the velocity and/or mean gradient of blood flow through the cardiovascular system. Imaging and risk assessments may have to be carried out regularly on the subject, in order to sufficiently monitor the condition of the portion of the circulatory system over a long period of time.

In a sizable number of cases, the risk assessment and imaging assessment may diverge, such that the assessment of the subject is graded differently in each method. Therefore, it may be unclear what the clinician should recommend. For example, the risk assessment may suggest there is an elevated health risk to the subject, and hence the clinician could recommend that the subject undergoes a medical procedure. However, the imaging assessments may suggest that the condition of the portion of the subject's circulatory system is not as severe as the risk assessment suggests; hence, the clinician could recommend that a medical procedure is unnecessary for the subject. The uncertainty concerning the grading of the portion of the subject's circulatory system may result in error-prone risk stratification or misdiagnosis.

In order to assist the clinician in grading the condition of the subject, automated analysis of an echocardiogram image has been proposed. A two-dimensional (2D) image frame is taken from the echocardiogram scan. This 2D image frame becomes the input for a trained model, such as an artificial neural network. In the training phase, the model is trained to assess the condition of the subject by obtaining several 2D training image frames and generating corresponding ground truth data for each 2D training image frame. Subsequently, in the inference phase, the trained model is able to output data that characterises the condition of the subject (that is, when the 2D image frame is input into the trained model). The aim is that the resulting output data provides an objective assessment of the condition of the portion of the circulatory system, to assist the clinician when grading the condition of the subject. However, an incorrect risk level may still be applied to a subject, or a subject may still be misdiagnosed.

SUMMARY OF THE INVENTION

It would be desirable to provide a method to more accurately assess the condition of the portion of the circulatory system. Assessing the condition of the subject may more broadly include determining the severity of a problem in the area of interest and/or determining a suitable course of action for the subject. It would be further desirable that the method could be implemented regularly on a subject over a long period of time, so that regular updates could be provided on the condition of the subject. The inventors have recognised that important information is contained within the temporal dynamics of the circulatory system. By analysing the condition of the subject over a duration of time, more accurate output data characterising the condition of the subject may be produced by a trained model. By designing methods and systems capable of utilising this temporal information, fewer errors may be made when diagnosing, or assigning a risk level to, the subject.

The invention is defined by the claims. According to an aspect of the invention there is provided a computer-implemented method for assessing an area of interest in the circulatory system of a subject, the method comprising:

obtaining a temporal sequence of ultrasound image frames of the area of interest;

obtaining one or more trained models;

inputting the temporal sequence of ultrasound image frames into the one or more trained models; and analysing the temporal sequence of ultrasound image frames, using the one or more trained models, to produce output data characterising a condition of the area of interest, wherein the output data characterises an extent of atherosclerosis or calcification of the area of interest, and wherein the area of interest is the aortic valve.

The ultrasound image frames in the temporal sequence may be analysed together (that is, jointly) by the one or more trained models, to produce the output data. In particular, the ultrasound image frames of the temporal sequence for a given subject may be analysed using the one or more trained models in one iteration of the method. This would contrast with—for example—a process in which individual ultrasound image frames were analysed separately, in repeated, independent iterations of analysis.

The method assesses an area of interest within the cardiovascular system of the subject, and more specifically, assesses an area of interest within the heart of the subject.

The obtained ultrasound image frames may comprise or consist of frames from an echocardiogram performed on the subject. The echocardiogram performed on the subject may be transthoracic or transoesophageal, for example.

The method may further comprise displaying the output data on a graphical user interface. Displaying output data on a graphical user interface may help to better convey the output data to the clinician. Moreover, the output data may be more accessible to the subject as a result of the graphical user interface.

The subject may be a patient—for example, a patient who is being assessed pre- or post-operatively. Alternatively, the subject may be a healthy individual—for example, a person having a routine health check-up, or being examined as part of a screening programme.

Also provided is a system for providing an assessment of an area of interest in the circulatory system of a subject, the system comprising a processor configured to:

obtain a temporal sequence of ultrasound image frames of the area of interest;

obtain one or more trained models;

input the temporal sequence of ultrasound image frames to the one or more trained models; and analyse the temporal sequence of ultrasound image frames, using the one or more trained models, to produce output data characterising a condition of the area of interest, wherein the output data characterises an extent of atherosclerosis or calcification of the area of interest, and wherein the area of interest is the aortic valve.

The system may further comprise any one or any combination of two or more of:

an ultrasound system, configured to generate the temporal sequence of the area of interest of the subject;

an input, configured to receive the temporal sequence;

an output, configured to output the output data produced by the processor;

a memory, configured to store computer program instructions; and a display, configured to display the output data.

The output data may comprise a numerical score. In one example, the numerical score may define the severity of the calcification of the area of interest: for example, a high numerical score may denote a large volume of calcified regions in the area of interest, while a low numerical score may denote a small volume of calcified regions in the area of interest. Alternatively, the output data characterising the extent of atherosclerosis or calcification of the area of interest could be a segmented image or a segmented temporal sequence of images. For example, the segmented image(s), may identify one or more calcified regions in the area of interest.

According to another aspect, there is provided a computer-implemented method of training a model for assessing an area of interest in the circulatory systems of subjects, the method comprising:

obtaining, for each of a plurality of training subjects, one or more temporal training sequences of ultrasound image frames of the area of interest in that training subject;

obtaining, for each of the plurality of training subjects, ground truth data characterising a condition of the area of interest for that training subject; and training the model based on the obtained temporal training sequences and the corresponding ground truth data, such that the model is trained to produce output data characterising the condition of the area of interest in any given subject, based on a temporal sequence of ultrasound image frames of the area of interest in that subject, wherein the output data characterises an extent of atherosclerosis or calcification of the area of interest, and wherein the area of interest is the aortic valve.

Also provided is a system for training a model for assessment of an area of interest in the circulatory systems of subjects, the system comprising a processor configured to:

obtain, for each of a plurality of training subjects, one or more temporal training sequences of ultrasound image frames of the area of interest in that training subject;

obtain, for each of the plurality of training subjects, ground truth data characterising a condition of the area of interest for that training subject; and train the model based on the obtained temporal training sequences and the corresponding ground truth data, such that the model is trained to produce output data characterising the condition of the area of interest in any given subject, based on a temporal sequence of ultrasound image frames of the area of interest in that subject, wherein the output data characterises an extent of atherosclerosis or calcification of the area of interest, and wherein the area of interest is the aortic valve.

The system may further comprise an input configured to receive the one or more temporal training sequences and corresponding ground truth data, for each of a plurality of training subjects. The system may further comprise an output configured to output a trained model, once the model has undergone a sufficient amount of training. The "sufficient" amount of training may be determined by a performance goal that the model must be able to achieve before being output as a trained model. The performance goal may be related to the accuracy of the output data produced by the model for a temporal training sequence input into the model. The accuracy of the output data produced by the model may be compared with the ground truth data corresponding to the temporal training sequence input into the model.

Each of the ultrasound image frames for the plurality of training subjects or the subject may be three-dimensional.

The 3D ultrasound image frames may be from 3D echocardiograms taken of the plurality of training subjects and/or the subject. 3D echocardiograms may be rotated, manipulated, or viewed from different perspectives by a clinician. The 3D ultrasound image frames are able to show the area of interest in three spatial dimensions, in contrast to a 2D ultrasound image frame from a 2D echocardiogram, which is restricted to two spatial dimensions. By forming the temporal sequence of three-dimensional (3D) ultrasound image frames, the temporal sequence is able to show the area of interest in three spatial dimensions and one temporal dimension. Volume rendering may be used to display the ultrasound image frames in three dimensions, wherein different colour maps can be used to provide depth to the ultrasound image frame. Alternatively, surface rendering may be used to display the ultrasound image frames in three dimensions by generating a solid surface model, if blood-tissue boundaries are known.

In other embodiments, the ultrasound image frames for the plurality of training subjects and/or the subject may comprise or consist of 2D images. 2D ultrasound image frames may capture a cross-sectional view of the area of interest. The cross-sectional view of the area of interest captured in the 2D images may be long axis or short axis, may be parasternal or may be apical.

Moreover, the inventors have recognised that the temporal dynamics of the circulatory system are periodic. Most (if not all) of the important information that can be obtained from imaging the circulatory system is captured within one periodic event; for instance, the repeating nature of the cardiac cycle means that most (or all) of the important information is captured within one heartbeat. The inventors have identified that methods and systems able to assess the condition of the portion of the circulatory system over at least one periodic event would be beneficial, in order to accurately assess the area of interest.

The obtained temporal sequence or each of the obtained temporal training sequences may have a duration greater than or equal to one period of a periodic event associated with the circulatory system.

Here, the term "duration" of the temporal sequence or temporal training sequences means the length of time over which the ultrasound image frames are captured. The duration may be directly measured in units of time, or in multiples of the period. The duration of one periodic event is equal to one period. The periodic event may be a heartbeat of the subject. The temporal sequence and/or the temporal training sequences of ultrasound image frames may have a duration less than two periods of the periodic event in the area of interest, optionally less than 1.5 periods, and optionally less than 1.2 periods. Limiting the duration of the temporal sequence and/or the duration of the temporal training sequences may avoid the need to record, store, and/or process duplicate data, which may arise from assessing an area of interest over a duration which spans multiple periods of the same periodic event.

The step of obtaining each temporal sequence of ultrasound image frames may comprise capturing the frames during an echocardiogram, or obtaining a sequence of ultrasound image frames captured during an echocardiogram. An echocardiogram may be used to obtain the temporal sequences and/or the temporal training sequences. The echocardiogram may be used by the operator to identify whether the obtained temporal sequence and the obtained temporal training sequences have a duration of at least one period.

In some embodiments, the temporal sequence and/or each of the temporal training sequences of ultrasound image frames may have a duration greater than or equal to two or more periods of the same periodic event associated with the circulatory system. A temporal sequence of a duration greater than or equal to two or more periods may be useful to identify differences or common features in the output data between different periods of the same periodic event for the subject.

The obtained temporal sequence or each of the obtained temporal training sequences may be aligned, such that it starts at the same predetermined point of a periodic event associated with the circulatory system.

For example, when the periodic event is a heartbeat, the temporal sequence and each temporal training sequence of frames may start at a predetermined point in the heartbeat, such as a P, Q, R, S, or T wave in an electrocardiogram (ECG). The obtained temporal sequence and each of the obtained temporal training sequences may be further aligned such that the temporal sequence and temporal training sequences may start at the same predetermined start point of the periodic event and may end at the same predetermined end point of the periodic event. For example, when the periodic event is a heartbeat, the temporal sequence and each temporal training sequence of frames may start at a P wave and end at an R wave in an electrocardiogram, each sequence having a duration greater than one period. Alternatively, the predetermined start point and predetermined end point of the periodic event may be the same, such that each sequence has a duration equal to one period.

The method may comprise pre-processing the obtained temporal training sequences to align them as defined above. The method may comprise pre-processing the obtained temporal sequence, to align it as defined above. Preferably, the temporal sequence, and each temporal training sequence, are all aligned in the same way. That is, they all start (and optionally end) at the same point(s) in the periodic event.

If the temporal training sequences are aligned in this way, it may be easier to train the model. By using aligned temporal training sequences, fewer temporal training sequences may be needed to train the model, as the variation between each temporal training sequence is reduced, compared with a plurality of unaligned temporal training sequences.

Alternatively, the obtained temporal sequence and temporal training sequences may start at different points of the periodic event; for example, one temporal training sequence may start and finish at an R wave, while a different temporal training sequence may start and finish at a P wave. More generally, the temporal sequence and each temporal training sequence may start and/or finish at an arbitrary point of the periodic event. By training a model to assess an area of interest using temporal training sequences that have not been aligned, output data characterising the area of interest can be produced for a temporal sequence starting from any point of the periodic event. If the temporal training sequences are not aligned, a larger number of temporal training sequences may be needed to train the model.

The aligned temporal sequence or each of the aligned temporal training sequences may have a duration greater than or equal to one period of the periodic event associated with the circulatory system.

Each obtained temporal sequence or each of the obtained temporal training sequences may have the same number of ultrasound image frames.

That is, the temporal sequence may have a number of ultrasound image frames N. Each temporal training sequence may have an identical number of ultrasound image frames N. The length of a temporal sequence and/or temporal training sequence is defined as the number of ultrasound image frames in the temporal sequence and/or temporal training sequence. In the example above, each temporal sequence and each temporal training sequence has length N.

The temporal sequence and/or the temporal training sequences may have a fixed frame rate, wherein a fixed duration of time passes between each ultrasound image frame contained in the temporal sequence and/or the temporal training sequences. For a temporal sequence and temporal training sequences that have a fixed frame rate, if the temporal sequence and temporal training sequences have the same length, they will also have an equal duration.

The obtained temporal sequence and the obtained temporal training sequences may each have a duration that is a fixed proportion of the period of a respective periodic event associated with the circulatory system.

For instance, each sequence may have a duration that is (for example) 1.2 times the period of the respective periodic event.

The obtained temporal sequence and obtained temporal training sequences may have a variable number of image frames, or in other words, a variable length. This may occur if the temporal sequence and temporal training sequences have a fixed frame rate, as the period of the periodic event may be different for each subject.

The obtained temporal sequence and/or each of the obtained temporal training sequences may have a duration greater than or equal to one period of the periodic event associated with the circulatory system.

The obtained temporal sequence and each of the obtained temporal training sequences may be aligned, such that the temporal sequence and/or temporal training sequences start at the same predetermined point of the periodic event associated with the circulatory system.

The model, or each model, may comprise a spatio-temporal fully convolutional neural network.

The use of a fully convolutional neural network can allow the trained model to produce output data characterising the condition of the area of interest in any given subject via end-to-end learning. By "end-to-end" learning, it is meant that the model learns to directly infer the output data (characterising the condition of the area of interest) from the input data (that is, the temporal sequence of ultrasound image frames), without the need for separate intermediate steps. For example, in some embodiments, a separate step of feature extraction (wherein the dimensionality of the input data is reduced before it is input into a second, separate model for classification or other inference) is not required.

The model, or each model, may comprise a convolutional neural network and a recurrent neural network working in series.

Here, "working in series" means that an input of one of the neural networks is based directly or indirectly on an output of the other neural network. In particular, a temporal sequence or temporal training sequence may be input to a 2D or 3D convolutional neural network. An output of the 2D or 3D convolutional neural network may become an input for the recurrent neural network, which subsequently produces output data characterising the condition of the area of interest.

When training a model, each ultrasound image frame from one of the one or more temporal training sequences may be input into the convolutional neural network. The convolutional neural network may output a feature vector for each ultrasound image frame in the temporal training sequence. In this case, the number of feature vectors produced for the temporal training sequence will vary, depending on the number of ultrasound sound image frames in the temporal training sequence. The extracted feature vectors may then be input sequentially into a recurrent neural network. The recurrent neural network may then produce the output data. The recurrent neural network may be a long short-term memory (LSTM) network, for example. Using the same convolutional neural network and recurrent neural network in the inference phase (that is, when providing an assessment of an area of interest of the circulatory system), each ultrasound image frame from the temporal sequence may be input into the trained model to produce output data.

The recurrent neural network may be capable of inference from sequences of variable length (at least when trained with training sequences of variable length). This property may be useful when using a fixed frame rate, and sequences whose duration depends on the period of the periodic event. Alternatively or in addition, it may be useful when using a variable frame rate (with sequences of fixed or non-fixed duration).

When the model comprises a recurrent neural network, training the model may comprise generating additional temporal training sequences based on the obtained temporal training sequences. At least some of the additional temporal training sequences may be generated by temporal resampling of the obtained temporal training sequences—for example, by decimation and or interpolation in time. This is a further example of augmenting the training data.

One or more first models may be trained to produce output data for a first set of subjects and one or more second models may be trained to produce output data for a second, different set of subjects.

As an example, the subjects may be split into a first set of subjects and a second set of subjects based on their sex. In this example, one or more first models may be trained using temporal training sequences obtained from male training subjects. Thus, these one or more first trained models would produce output data for male subjects. Likewise, one or more second models may be trained using temporal training sequences obtained from female training subjects, so that the one or more second trained models are trained to produce output data for female subjects. The subjects may be split into other sets of subjects based on certain demographics, such as age, body mass index, physical activity level, diet, or smoking status. More than two different sets of subjects may exist; for example, there may exist one or more third models, which are trained to produce output data for a third set of subjects.

The inventors have further recognised that it would be desirable if methods and systems could predict a likelihood of certain events happening after a medical procedure takes place (for example, if the risk level of the subject is high enough for a medical procedure to be recommended). Non-limiting examples of these likelihoods could include a prediction of all-cause mortality following the medical procedure, or a predicted likelihood of further medical procedures being required. Such procedural outcome predictions may form part of the assessment of the condition of the subject. Producing more detailed output data describing the condition of the subject may help the clinician to deliver a more accurate and well-rounded assessment of the condition of the subject.

The output data may comprise any one or any combination of two or more of the following:

a prediction of a score describing the severity of a problem in the area of interest;
  a predicted likelihood of survival of the subject;
  a prediction of procedural success;
  a prediction of continued success post-procedure;
  a predicted likelihood of a subject requiring a pacemaker post-procedure; and
  a segmentation of at least one obtained ultrasound image frame, indicating at least one region of the area of interest in a subject.

The output data produced by one trained model might only comprise one item of output data listed above. Multiple trained models may each produce one different item of output data listed above. Alternatively, one trained model may produce multiple items of output data listed above.

If the condition of the area of interest is poor, there may be a problem in the area of interest. For example, the problem may be calcification in the area of interest.

Here, the term "procedural success" means that the medical procedure has been successful, such that the condition of the area of interest improves as a result of the medical procedure.

Here, the term "post-procedure" means "at a time after a medical procedure has been performed on a subject" (the medical procedure having been performed in order to improve the condition of the area of interest of the subject). Producing output data that predicts procedural outcomes may help to guide a clinician when deciding whether the medical procedure should go ahead, or may help the clinician to decide whether there is a need for additional treatment after the procedure.

The term "continued success post-procedure" means that once "procedural success" is achieved, the condition of the area of interest remains improved as a result of the medical procedure. If a prediction of continued success post-procedure is low, the clinician may advise the subject that the medical procedure is unlikely to be of long-term benefit.

If the method produces output data that characterises an extent of calcification of the aortic valve, the medical procedure may comprise or consist of a transcatheter aortic valve replacement (TAVR).

The segmentation of the at least one obtained ultrasound image frame may be generated from a saliency map via thresholding to indicate at least one region of the area of interest. The saliency map may be generated using a back-propagation algorithm, optionally using a guided backpropagation algorithm, or optionally using a guided Grad-CAM backpropagation algorithm. Other suitable algorithms for saliency-map generation may also be used. The segmentation of at least one ultrasound image frame may better indicate the at least one region of the area of interest in the subject, to the subject or the clinician, compared with the at least one ultrasound image frame. The segmentation may comprise a segmentation map identifying the at least one region.

The segmentation of the at least one obtained ultrasound image frame may be generated by inputting the at least one ultrasound image frame into the one or more trained models. The one or more trained models may have been trained to produce a segmented image of the at least one ultrasound image frame (indicating the at least one region of interest in the subject) as output data, based on one or more ultrasound image training frames and the corresponding ground truth data (segmented training images of the ultrasound image training frames). Examples of a trained model suitable for image segmentation include U-Net, a convolutional neural network designed to segment a 2D image, and 3D U-Net, a convolutional neural network designed to segment a 3D image.

The output data may comprise any one or any combination of two or more of the following:

a prediction of an AVC score describing the severity of the calcification;

a predicted likelihood that the TAVR is successful;

a prediction of continued success post-TAVR;

a predicted likelihood of a subject requiring a pacemaker post-TAVR;

a segmentation of at least one obtained ultrasound image frame, indicating at least one calcified region of the area of interest in a subject;

a predicted likelihood of a paravalvular leak; and a prediction of all-cause mortality.

The aortic valve calcification (AVC) score may be represented by a binary classification output: the area of interest may be classified as normal if the amount of calcification is low, and may be classified as elevated if the amount of calcification is high.

Alternatively, the AVC score may define degrees of uncertainty beyond a binary classification output. A non-binary description of the severity of the calcification may help to categorise subjects who are close to the classification boundary between the normal and elevated classifications. For example, the area of interest may be classified as 'slightly elevated' if the amount of calcification is close to the boundary between the normal and elevated classifications.

The AVC score may comprise or consist of a predicted Agatston score. By being able to predict metrics that are traditionally derivable only from CT scans, such as the Agatston score, also known as CT aortic valve calcium scoring, the condition of the area of interest can be characterised by a well-known and used metric, without requiring a CT scan. This can make the present method more suitable for regular monitoring of a subject, over time. A regular echocardiogram may pose a lower risk to the subject than an equally frequent CT scan, because the CT scan involves irradiating the subject with X-rays. In order to produce a predicted Agatston score as output data, the method may comprise obtaining temporal training sequences and the corresponding ground truth data (the corresponding Agatston scores for each of the plurality of training subjects). This may comprise determining the Agatston scores corresponding to each of the temporal training sequences from a CT scan, taken of the area of interest for each training subject.

The prediction of all-cause mortality estimates the likelihood of the subject dying (irrespective of the cause of death) within a predetermined time period, based on the content of the temporal sequence of ultrasound image frames.

A "prediction of continued success post-TAVR" is an item of output data that predicts the likelihood of the TAVR being successful in improving the condition of the aortic valve of the subject, and the likelihood that, in the future, the condition of the aortic valve does not significantly deteriorate to the point that additional medical procedures are required to improve the condition of the aortic valve. Markers such as the predicted likelihood of paravalvular leakage, the predicted likelihood of a subject permanently requiring a pacemaker post-TAVR, and the prediction of procedural success may be used to produce a prediction of continued success post-TAVR.

The output data may comprise one or more numerical scores, such as may be produced by a regression-type trained model. Alternatively or in addition, the output data may comprise a classification into one of a number of categories (which may be mutually exclusive), such as may be produced by a classification-type trained model. Thus, for example, a predicted AVC score may comprise a numerical score generated by a regression model, or may comprise a classification (such as "normal", "slightly elevated", or "elevated") generated by a classification model. When the output data comprises a numerical value, a classification may be generated in a post-processing step, by comparing the numerical value to one or more threshold levels.

Also provided is a computer program comprising computer program code configured to cause at least one physical computing device to carry out all the steps of the method of any one of the claims if said computer program is executed by said at least one physical computing device. The computer program may be stored on a computer readable storage medium (optionally a non-transitory computer readable storage medium).

BRIEF DESCRIPTION OF THE DRAWINGS

The invention will now be described by way of example with reference to the accompanying drawings, in which.

Figure 1:
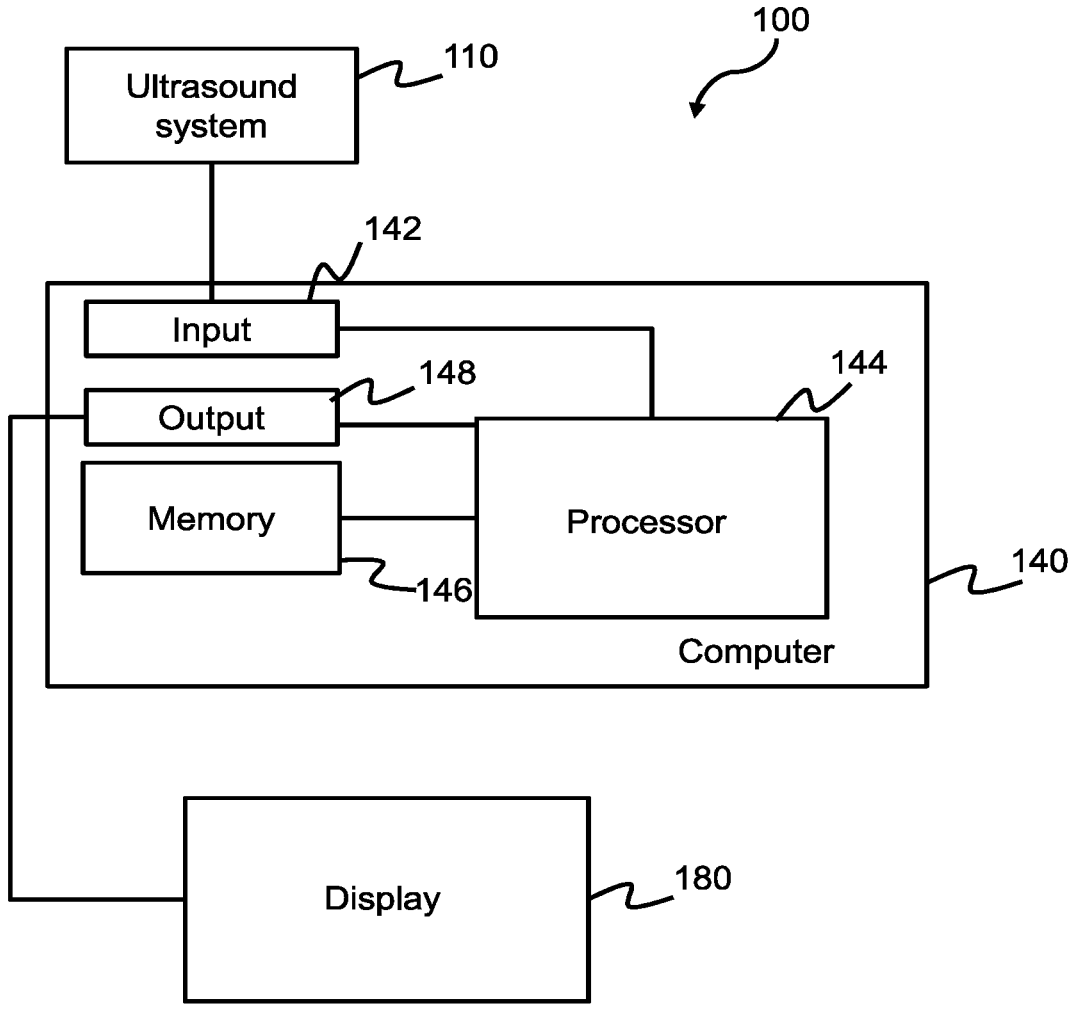
FIG. 1 is a schematic block diagram of a system for providing an assessment of an area of interest in the circulatory system of a subject.

It should be noted that these figures are diagrammatic and not drawn to scale. Relative dimensions and proportions of parts of these figures have been shown exaggerated or reduced in size, for the sake of clarity and convenience in the drawings.

DETAILED DESCRIPTION OF THE EMBODIMENTS

Reference will now be made in detail to embodiments of the invention, examples of which are illustrated in the accompanying drawings. The described embodiments should not be construed as being limited to the descriptions given in this section; the embodiments may have different forms. These and other features, aspects, and advantages of the apparatus, systems and methods of the present invention will become better understood from the following description, appended claims, and accompanying drawings. It should be understood that the same reference numerals are used throughout the Figures to indicate the same or similar parts.

FIG. 1 illustrates a system 100 for providing an assessment of an area of interest in the circulatory system of a subject being assessed. The subject may be a healthy individual, undergoing the assessment as part of a routine health check-up, or may be a patient, who is being assessed pre-operatively or post-operatively. The system in this example comprises an ultrasound system 110 to generate a temporal sequence of ultrasound image frames of the area of interest of the subject, a computer 140, and a display 180. The computer 140 comprises a processor 144 configured to obtain the temporal sequence and one or more trained models, input the temporal sequence to the one or more trained models, and analyse the temporal sequence using the one or more trained models to produce output data characterising a condition of the area of interest. The computer 140 also comprises an input 142 configured to receive the temporal sequence, a memory 146 configured to store computer program instructions, and an output 148 configured to output the output data produced by the processor 144. The display 180 is configured to display the produced output data.

According to the present example, the system 100 is configured to provide an assessment of an aortic valve of the subject. That is, the "area of interest" in this example is the aortic valve. The processor 144 is configured to analyse the temporal sequence using the one or more trained models, to produce output data characterising an extent of calcification of the aortic valve.

Aortic valve calcification (AVC) can cause the opening of the aortic valve to narrow. This may lead to reduced blood flow through the aortic valve (aortic valve stenosis), if the AVC is severe. By characterising the extent of calcification of the aortic valve of the subject, a clinician is able to apportion a risk level to the subject. Stratifying multiple subjects according to their risk level optimizes quality of care for the subjects, prioritising greater resources for those who need it most (the subjects in the higher risk levels). For example, a transcatheter aortic valve replacement (TAVR) procedure is commonly used to repair non-functioning aortic valves, in particular valves that fail to open properly, so that blood flow is restored from the left ventricle to the aorta. The TAVR procedure may be suitable for subjects who have a high risk level. By characterising the extent of calcification of the aortic valve of the subject, the system can inform the clinician about the risk level of the subject and help the clinician to determine whether subjects require a TAVR or a similar medical procedure, whether subjects would suffer undue complications as a result of a TAVR, and/or whether subjects would require particular post-operative care.

Figure 2A:
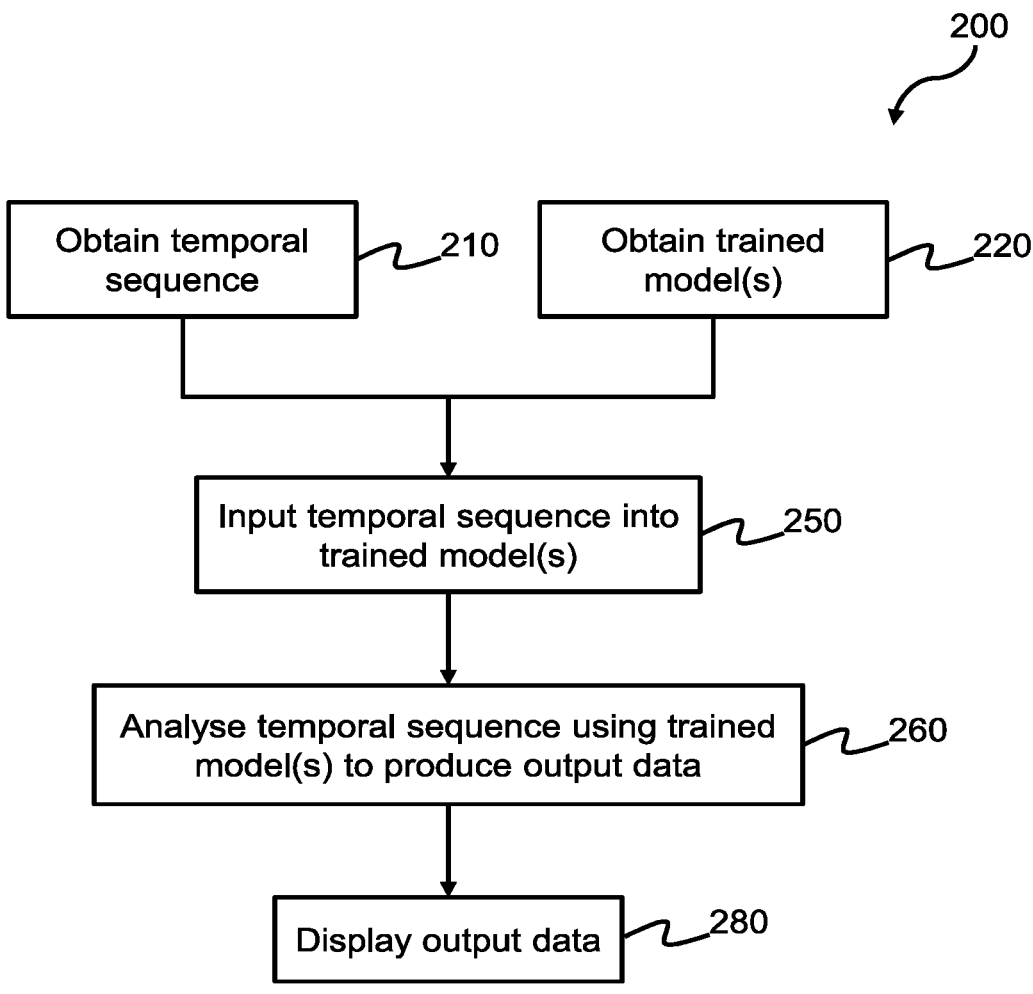
FIG. 2A is a flowchart, illustrating a method for assessing an area of interest in the circulatory system of a subject.

FIG. 2A is a flowchart illustrating a method 200 for assessing an area of interest in the circulatory system of a subject, according to a first example. In the present example, as explained above, the area of interest is the subject's aortic valve. In step 210, the processor 144 obtains a temporal sequence of ultrasound image frames of the aortic valve from the ultrasound system 110, via the input 142. In this example, the temporal sequence of ultrasound image frames consists of 2D image frames of an echocardiogram taken of the subject, using the ultrasound system 110.

The temporal sequence has a duration (defined as the temporal duration in which the ultrasound image frames are captured) which is greater than or equal to one period of a periodic event associated with the circulatory system. In this example, the periodic event is the heartbeat of the subject, such that the temporal sequence has a duration that spans at least one heartbeat. This can be achieved by monitoring the heartbeat of the subject using an electrocardiogram (ECG), determining the heartrate from the ECG, and capturing the temporal sequence at the ultrasound system such that the duration of the temporal sequence is selected to be equal to (or slightly greater than) the period of the heartbeat.

The temporal sequence is assumed to have a constant, predetermined frame rate (which may be determined by the capabilities of the ultrasound system 110). Since the heartrates of different subjects are liable to be different, this means that the temporal sequence will in general contain a variable number of frames—that is, it will be a sequence of variable length.

In step 220, the processor 144 obtains one or more trained models from the memory 146. The one or more trained models are artificial neural networks which have been trained to assess the condition of the aortic valve of the subject based on the temporal sequence obtained in step 210. More specifically, in this example, each of the trained models comprises a convolutional neural network (CNN) and a recurrent neural network (RNN) working in series. By "working in series", it is meant that the input of one of the neural networks is based directly or indirectly on the output of the other neural network. In particular, the temporal sequence is input to the convolutional neural network. The output of the convolutional neural network provides the input for the recurrent neural network, which subsequently produces output data characterising the extent of calcification of the aortic valve. Such a model may be useful for analysing temporal sequences of variable length.

In the present example, each individual ultrasound image frame of the temporal sequence is input separately into the convolutional neural network, which acts as a feature extractor, producing feature vectors as output for each ultrasound image frame. The extracted feature vectors are then input sequentially into the recurrent neural network, which produces the output data. As the feature vectors are input sequentially into the recurrent neural network, the length of the temporal sequence or of each of the temporal training sequences does not have to be fixed. The recurrent neural network used in the present example is a long short-term memory (LSTM) network. This type of model may be useful when using sequences with a fixed frame rate whose duration depends on the period of the periodic event. Note that there is no need for any particular alignment of the temporal sequences of different subjects. In the present example, it is assumed that the temporal sequence may start and end at arbitrary points in the cardiac cycle—that is, arbitrary points or phases of the heartbeat—provided that the duration of the sequence lasts for at least one heartbeat.

The convolutional neural network used as the feature extractor could be one of a number of types. Existing networks for feature extraction, such as VGG16, VGG19, or GoogLeNet (pre-trained, for example, on the ImageNet dataset) may be used. Alternatively, a bespoke feature extraction neural network could be trained specifically for extracting features from ultrasound image frames.

According to the present example the model is not trained via end-to-end learning. That is, the convolutional neural network used for feature extraction is trained separately from the recurrent neural network that produces the output data. (However, it should be understood that, in other examples, end-to-end learning may be applied, wherein the convolutional neural network and recurrent neural network are trained together.)

In step 250, the processor 144 inputs the temporal sequence obtained in step 210 into the one or more trained models obtained in step 220. The processor analyses the temporal sequence using the one or more trained models, to produce output data characterising the extent of calcification of the aortic valve (step 260).

The output data produced by analysing the temporal sequence (using the one or more trained models) provides information to the clinician about the extent of the calcification of the aortic valve. The output data may comprise one of, or any combination of: an AVC score that describes AVC severity, a predicted likelihood of the subject requiring the a TAVR procedure, a predicted likelihood that the TAVR procedure is successful, a prediction that the TAVR procedure is successful for the expected lifespan of the TAVR, a predicted likelihood of a subject requiring a pacemaker post-after the TAVR, a predicted likelihood of a paravalvular leak, and a segmentation of at least one obtained ultrasound image frame indicating at least one calcified region in the aortic valve. One suitable neural network for producing a segmentation is U-Net. In the present example, each ultrasound image frame may be processed and segmented separately.

In this way, the method 200 is not only able to produce output data that quantifies the condition of the aortic valve, and the extent of the calcification, but is also able to produce output data that predicts TAVR procedural outcomes. Hence, when assessing the aortic valve of the subject, the clinician is able to use output data produced by the method 200 to assign a more accurate risk level to the subject, in part by factoring in predicted TAVR procedural outcomes.

In step 280, the processor 144 displays the output data produced on the display 180. This communicates the output data to the clinician, and may also help the clinician to convey information to the subject.

Figure 2B:
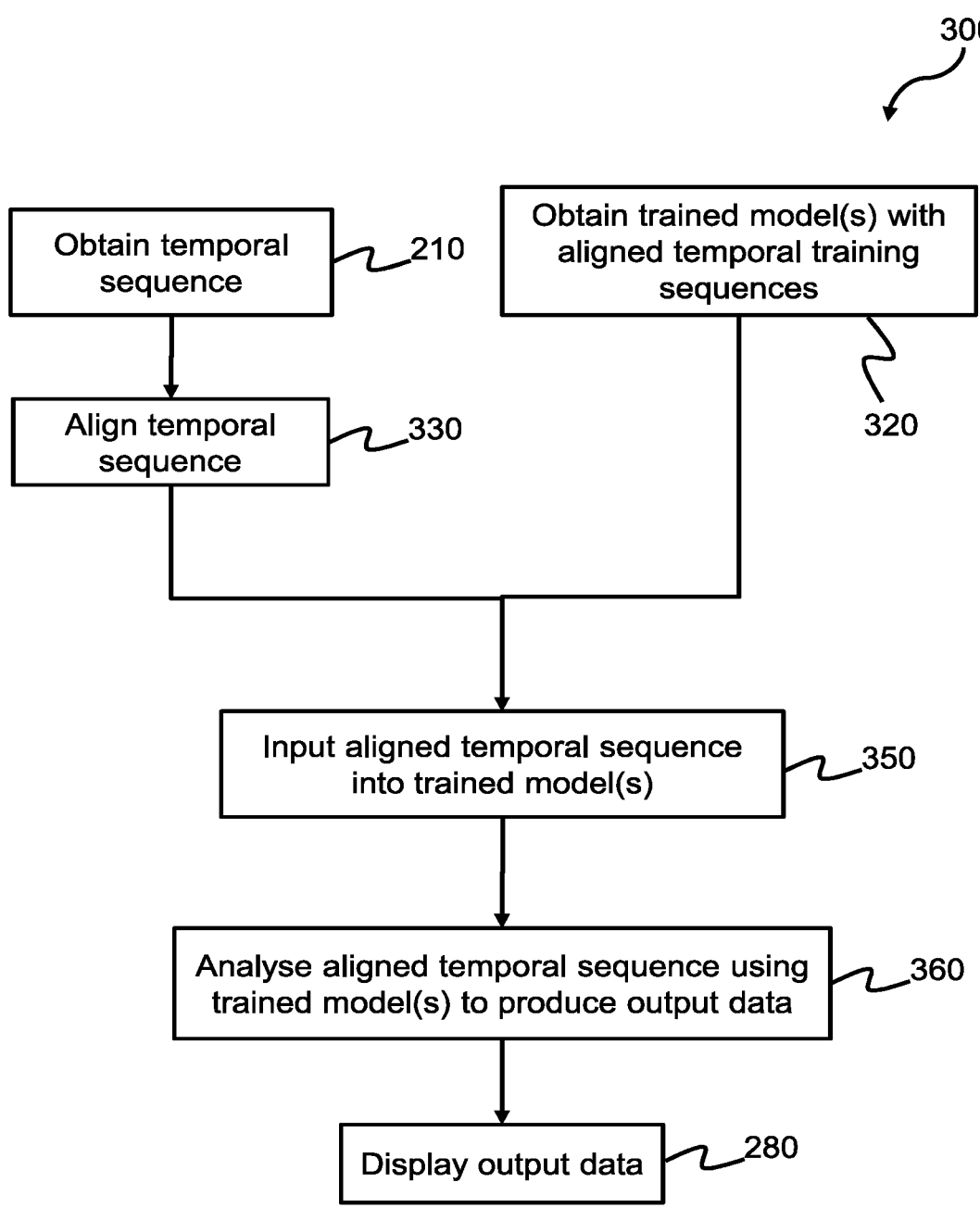
FIG. 2B is a flowchart illustrating the method for assessing the area of interest in the circulatory system of the subject, in which the method further comprises aligning a temporal sequence.

FIG. 2B is a flowchart illustrating a method 300 for assessing the condition of an aortic valve of a subject, according to a second example. The method 300 is similar in many ways to the methods 200 of FIG. 2A. Step 210 is common to both methods—the processor 144 obtains a temporal sequence of ultrasound image frames of the aortic valve of the subject. In general, the temporal sequence is of variable length and may start and finish at arbitrary points in the cardiac cycle. However, it is assumed, once again, that the duration of the temporal sequence is greater than or equal to the period of the heartbeat.

In step 330, the processor 144 aligns the temporal sequence such that it starts at a predetermined point of the heartbeat of the subject. This may be done using image processing techniques to identify the desired point of the heartbeat, or it may be based on additional side-information, such as ECG data that identifies different parts of the heartbeat. In the present example, the processor 144 aligns the temporal sequence such that it contains exactly one heartbeat, starts and ends at a predetermined point of the heartbeat, and has a predetermined number of image frames. To do this, the processor 144 shifts and scales the ultrasound image frames in the temporal dimension, to achieve the desired alignment. (Scaling in the temporal dimension may comprise decimation in time or interpolation in time, for example.) The result of this step is an "aligned" temporal sequence, which has a fixed length (that is, it contains a fixed number of frames), and which starts and ends at a consistent predetermined point of the heartbeat. The predetermined point may be defined by reference to parts of the ECG—for example, the predetermined point may correspond to a P, Q, R, S, or T wave of the ECG.

In step 320, the processor 144 obtains one or more trained models from the memory 146. The trained models in this example differ from those used in the method 200 of FIG. 2A. Here, the aligned temporal sequence, produced in step 330, provides input data to the one or more trained models in a uniform format. This may allow greater flexibility in the selection of the type of model. It can also reduce the burden on the trained models to adapt to input data representing the heartbeat in variable phases of the cardiac cycle, and input data of variable length.

In this example, each of the trained models is a spatio-temporal fully convolutional neural network. Spatio-temporal networks are able to analyse both the spatial patterns within the image frames and the temporal dependencies between them. The underlying idea of using such networks is that, motion, flow, and dynamics carry information about the nature of the sequence at hand.

In step 350, the processor 144 inputs the aligned temporal sequence produced in step 330 into the one or more trained models obtained in step 320. The processor analyses the aligned temporal sequence using the one or more trained models, to produce output data characterising the extent of calcification of the aortic valve (step 360). In step 280, as in the method 200, the processor 144 displays the output data produced on the display 180.

Figure 3:
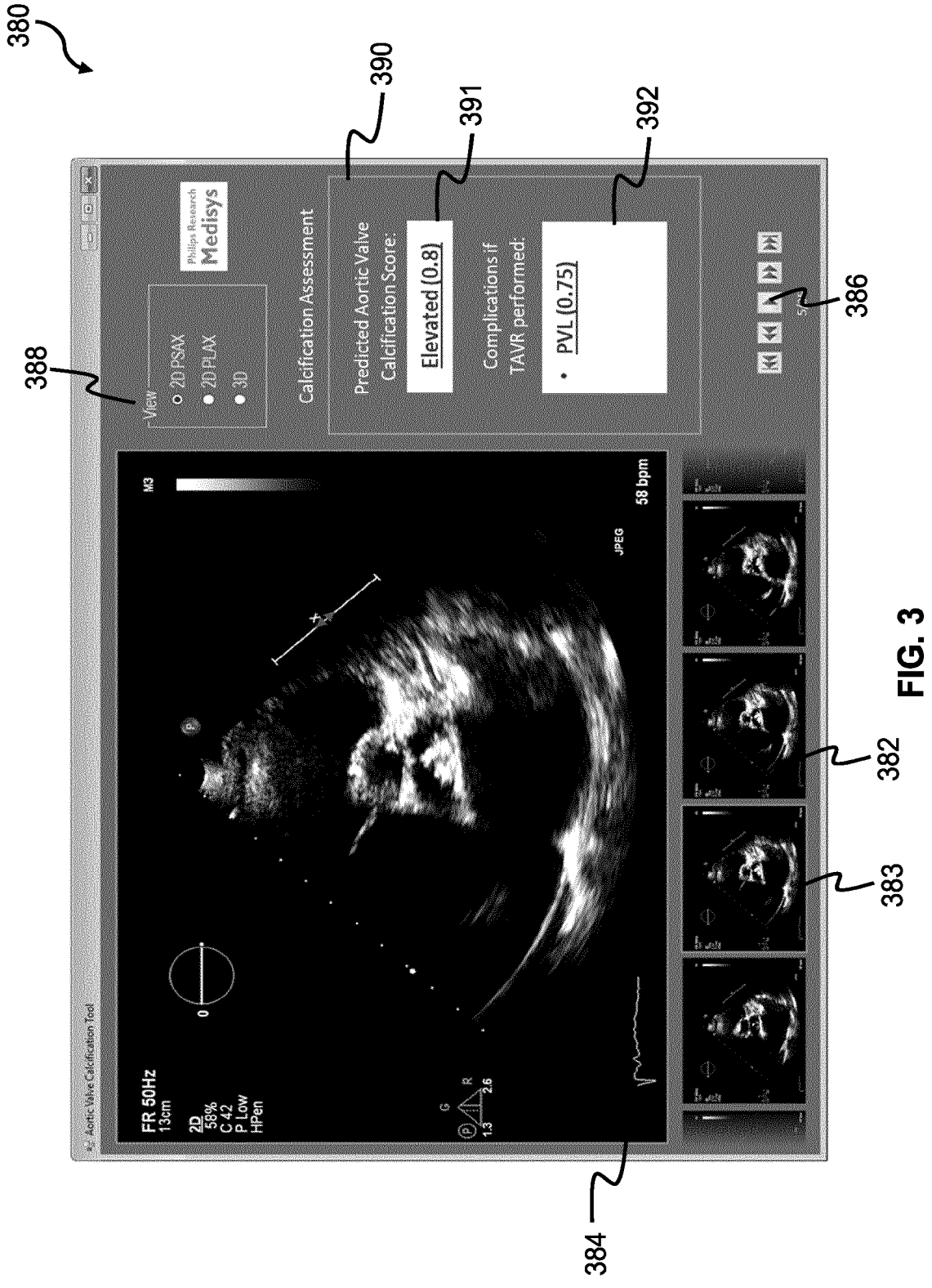
FIG. 3 is an example of a display on a graphical user interface, showing output data produced by the method for assessing the area of interest.

FIG. 3 shows an example of a graphical user interface 380 displayed on the display 180. This graphical user interface 380 can be used to show output data produced in a method like that of FIG. 2A or 2B. In the example of FIG. 3, the output data is presented together with the temporal sequence of ultrasound image frames. Individual thumbnail frames

382, 383 of the temporal sequence are shown along the bottom of the screen. One frame 383 has been selected by the clinician, and an enlarged version 384 of this frame is shown above the thumbnail frames 382, 383. Playback controls 386 are provided, to allow the clinician to navigate through the temporal sequence—for example, to play, pause, fast-forward, or rewind.

In the top right of the graphical user interface 380, radio buttons 388 allow the clinician to change the view of the temporal sequence. For example, the clinician can choose whether to display the temporal sequence in two spatial dimensions, or three spatial dimensions. Moreover the clinician can choose how to view the aortic valve of the subject, if inspecting the condition of the aortic valve in two spatial dimensions. For example, the clinician could select '2D PLAX', to display a parasternal long-axis view of the aortic valve, or could select '2D PSAX', to display a parasternal short-axis view of the aortic valve.

On the right hand side of the graphical user interface 380, a box 390 labelled "calcification assessment" displays output data produced by the processor 144 according to the method of FIG. 2A or 2B. In this example, it is assumed that the output data comprises an Agatston score and a prediction of procedural success. The processor produces the Agatston score by analysing the temporal sequence of ultrasound frames—for example, using a regression-type machine-learning model. The processor compares the Agatston score with a threshold and displays an indication 391 of whether the score is "elevated" (as shown in FIG. 3) or "normal". Also displayed is an optional confidence parameter in the assessment ("0.8"). The prediction of procedural success is presented as an indication 392 of a predicted risk of complications if a TAVR procedure is performed. In the example shown in FIG. 3, the system has assessed the subject as having a 75% chance of a paravalvular leak (PVL).

In another example, instead of explicitly producing a numerical Agatston score using a regression-type machine-learning model, the processor may use a classification-type machine-learning model to directly predict a stratified risk level. For example, the method may use a model that is trained to classify whether the predicted Agatston score is "elevated" or "normal". Of course, the classification need not be binary—a more detailed classification/stratification could be used, such as "elevated", "slight elevated", or "normal", for example.

In other examples, as mentioned above, the output data of the method may include a segmentation of one or more ultrasound image frames, indicating at least one region of calcification of the aortic valve. In this case, the segmentation may be displayed on the graphical user interface 380, as well as, or instead of, the ultrasound image frames 382, 383, 384 themselves.

Figure 4A:
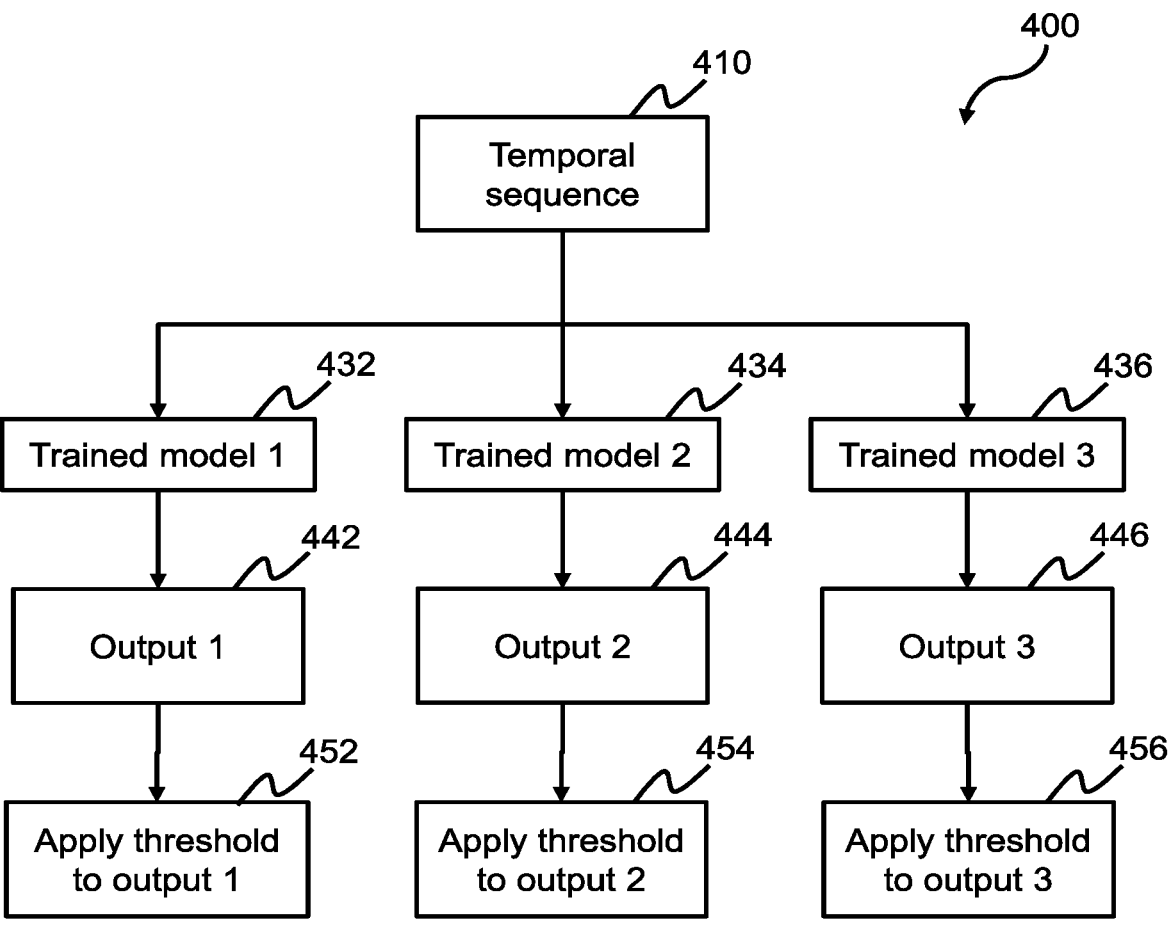
FIG. 4A is a flowchart illustrating an example of a method for assessing the area of interest, wherein multiple trained models produce output data for the subject.

FIG. 4A illustrates an example in which a temporal sequence 410 is analysed using multiple trained models 432, 434, 436 to produce multiple outputs 442, 444, 446. Each trained model comprises a neural network. A first trained model 432 analyses the temporal sequence 410 to produce a first output 442; a second trained model 434 analyses the temporal sequence 410 to produce a second output 444; and a third trained model 436 analyses the temporal sequence 410 to produce a third output 446. In one example, the first output 442 may comprise an AVC score; the second output may comprise a predicted likelihood of a paravalvular leak; the third output may comprise a predicted likelihood that the subject will survive for a predetermined time period following a TAVR procedure (for example, a prediction of all-cause mortality). In step 452, the processor 144 applies a first predetermined threshold to the first output 442. Likewise, in steps 454 and 456 the processor applies second and third predetermined thresholds to the second and third outputs 444 and 446, respectively. These thresholds can be used to stratify risk levels according to a binary classification—for example, assessing each output as representing a "high" or "low" risk. In other examples, more than one threshold may be applied to each output, in order to produce a non-binary classification of risk.

In some examples, multiple different trained models, may be used to analyse temporal sequences of different sets of subjects. For example, one model may be trained for male subjects and another model may be trained for female subjects. These two trained models may both be trained to produce the same output data—for instance, an AVC score. This can allow the analysis to be tailored to the characteristics of the different sets of subjects. For example, the average size of the aortic valve may be larger for one set of subjects than the other set of subjects. It should be understood that the example of training different models dependent on the sex of the subject is non-limiting. Demographic attributes other than sex may also be useful. For example, different models might be trained for subjects with specific risk factors, such as smokers, subjects with high body-mass index, etc.

Figure 4B:
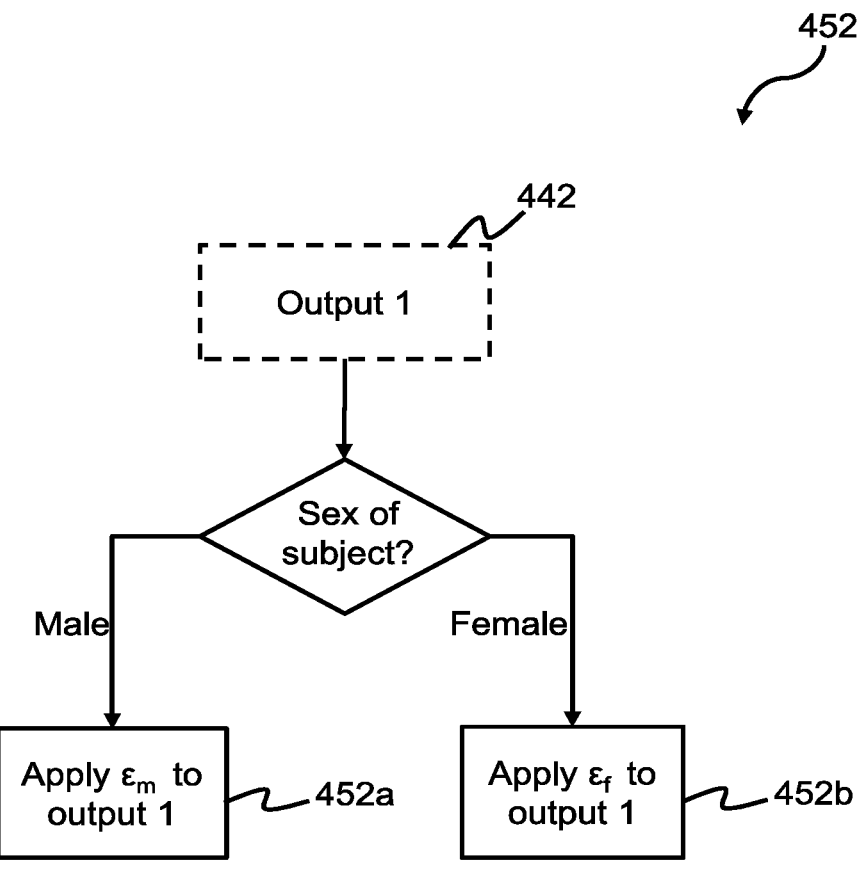
FIG. 4B is a decision tree showing how different thresholds may be applied to the output data.

As an alternative, or in addition, to training different models for different sets of subjects, different thresholds may be applied for the different sets of subjects. FIG. 4B illustrates an example of two different thresholds being applied in step 452. In this example, the sex of the subject has an effect on the risk level allocated to the subject. Different thresholds are applied to the subject, depending on the sex of the subject. As shown in FIG. 4B, a threshold value $\varepsilon_m$ is applied to the first output 442 if the subject is male in step 452a, and a threshold value $\varepsilon_r$ is applied to the first output 442 if the subject is female in step 452b. If the output 442 is an AVC score, the threshold values $\varepsilon_m$ and $\varepsilon_f$ may discriminate between elevated and normal calcification, for male and female subjects, respectively. By way of example, the threshold value may be higher if the subject is male than if the subject is female—that is, $\varepsilon_m$ may be greater than $\varepsilon_r$. This difference in threshold value, dependent on the sex of the subject, allows the risk level of the subject to be more accurately determined, based on the characteristics of the subject. This example is again non-limiting; there may be demographics, other than the sex of the subject, which have different associated threshold values in order to obtain an accurate risk level for the subject.

The training of the models used in the methods described above will now be described, with reference to FIGS. 5 and 6A-6C.

Figure 5:
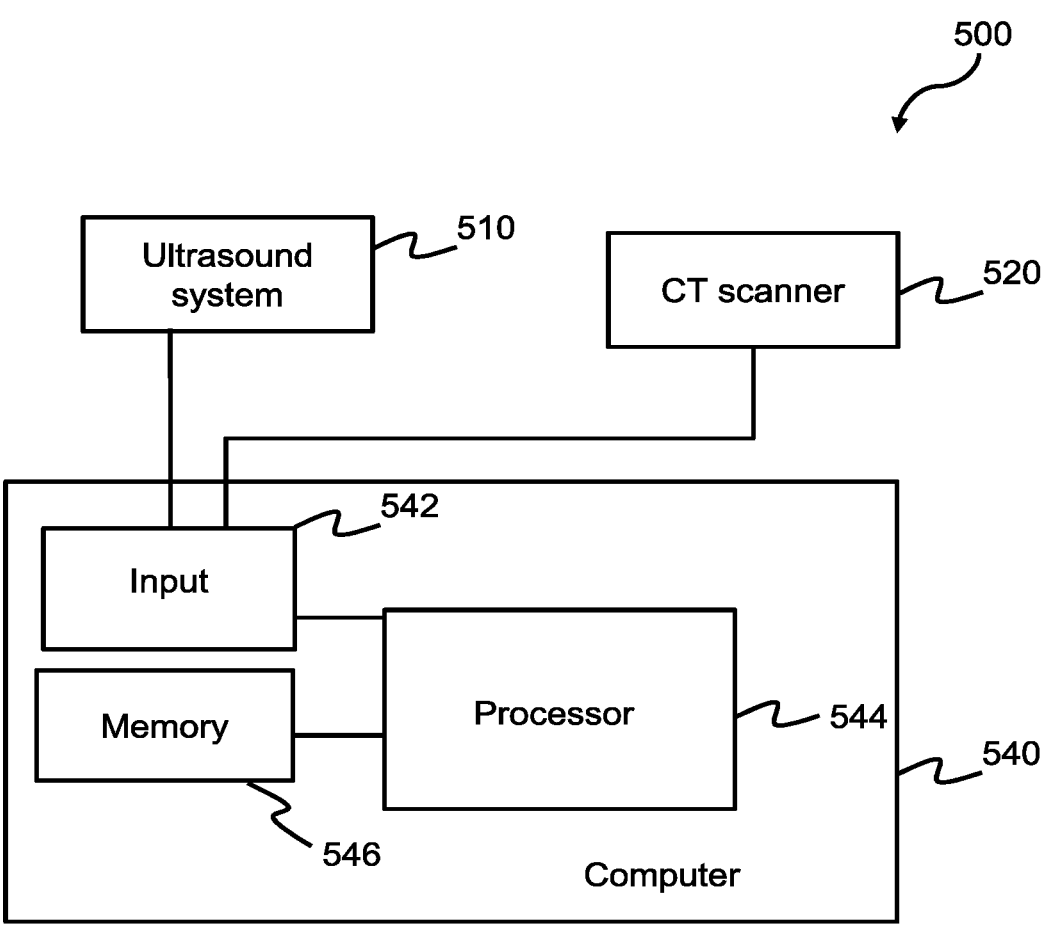
FIG. 5 is a schematic block diagram of a system for training a model for assessment of an area of interest in the circulatory systems of subjects.

FIG. 5 illustrates a system 500 for training a model for assessment of aortic valves of subjects. In particular, the system 500 in this example is for training the model to assess the extent of calcification of aortic valves. The system 500 comprises an ultrasound system 510, configured to generate one or more temporal training sequences of ultrasound image frames of the aortic valves of a plurality of training subjects. (One or more temporal training sequences may be generated per training subject.) The system 500 further comprises a CT scanner 520 and a computer 540. The CT scanner 520 is configured to capture CT scan data for use in generating ground truth data for the training process. The computer 540 comprises an input 542, a processor 544, and a memory 546. The processor 544 is configured to obtain the one or more temporal training sequences, to obtain the corresponding ground truth data, and to train the model. The input 542 is configured to receive the one or more temporal training sequences, the corresponding ground truth data, and the CT scan data. The memory 546 is configured to store computer program instructions. The system may further comprise an output configured to output the trained model.

Figure 6A:
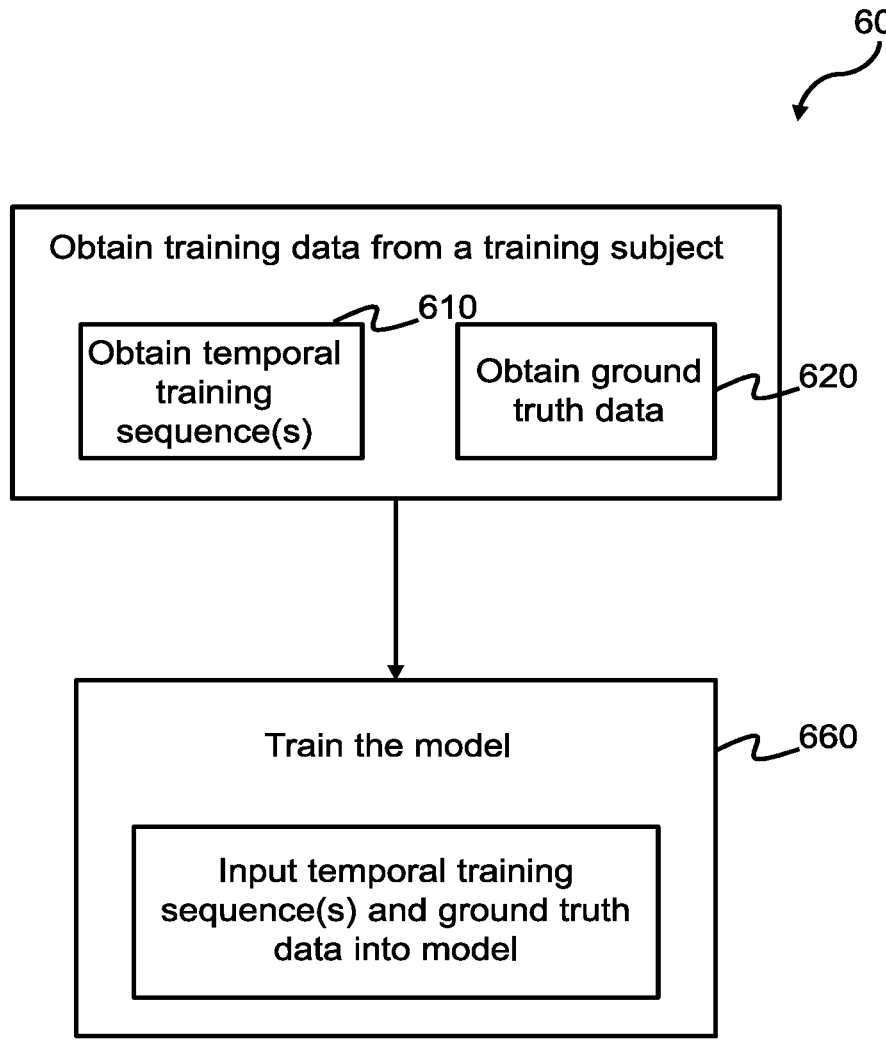
FIG. 6A is a flowchart illustrating a method of training a model for assessing an area of interest in the circulatory systems of subjects.

FIG. 6A illustrates a computer-implemented method 600 of training a model for assessing the extent of calcification of the aortic valve, using the system 500. The training method uses training data obtained from the plurality of training subjects. The training data includes temporal training sequences and corresponding ground truth data. In step 610, the processor 544 obtains the temporal training sequences from the ultrasound system 510 via the input 542. In step 620, the processor 544 obtains the corresponding ground truth data.

The temporal training sequences of ultrasound image frames in this example are from 2D echocardiograms taken of each training subject by the ultrasound system 510. Each temporal training sequence shows the aortic valve in two spatial dimensions and one temporal dimension. In this example, the training method will be used to train models suitable for use in the method of FIG. 2A. Therefore, the temporal training sequences are of the same kind as the temporal sequences that will be input to the inference method 200 in FIG. 2A. The temporal training sequences include a variety of lengths, and include sequences that start and end at arbitrary points in the heartbeat of the respective training subject.

In some examples, each of the temporal training sequences may comprise a different echocardiogram of a given training subject. However, because of the need for large quantities of training data, and the cost and/or difficulty of obtaining real echocardiogram data with associated ground truth, it may be advantageous to augment the training data with additional temporal training sequences derived from the original echocardiograms. For example, for a given original echocardiogram, multiple different temporal training sequences may be generated artificially by temporally shifting and/or scaling the echocardiogram in different ways. This may help to increase the variety of training data, which, in turn, may help the model to learn to deal with greater variability in the input data to the inference method.

The ground truth data obtained in step 620 comprises an AVC score for each of the training subjects. In the present example, it will be assumed that the AVC score is an Agatston score. Therefore, the ground truth is produced by expert (clinician) analysis of the CT scan data of the same training subject. In some other examples, the ground truth data may be produced by automated analysis of the CT scan data, by means of another trained machine learning algorithm. It should be understood that the ground truth data corresponds to the output data that the model is to be trained to produce. Thus, if the model is to be trained to produce other outputs, such as predictions of procedural outcomes, then the ground truth data may be actual outcomes of procedures performed on the training subjects after the temporal training sequences were generated. Alternatively, the ground truth data may comprise expert (clinician) predictions of procedural outcomes. If the output data comprises a segmentation of at least one ultrasound image frame, then the ground truth data may comprise a ground truth segmentation indicating at least one region of calcification of the aortic valve of each training subject.

In step 660, the processor 544 trains the model based on the temporal training sequences and the corresponding ground truth data. The model is thereby trained to produce output data characterising the extent of calcification of the aortic valves of subjects. As explained above, with reference to FIG. 2A, the model comprises a neural network—in particular a CNN in series with an RNN (in particular, an LSTM). The CNN may be a generic feature extraction network, as explained above, or a specifically trained feature extractor designed for ultrasound image datasets. The RNN may be trained to analyse aortic valve calcification based on the features extracted by the CNN. Methods such as the backpropagation algorithm, for training neural networks, will be well known to those skilled in the art. The training is repeated for each model that needs to be trained—for example, the training process would be repeated for each of the models 432, 434, 436 in FIG. 4A, using appropriate ground truth data, to train the respective model to produce the desired output data. The trained models produced in step 660 are output for use in the method of FIG. 2A.

Figure 6B:
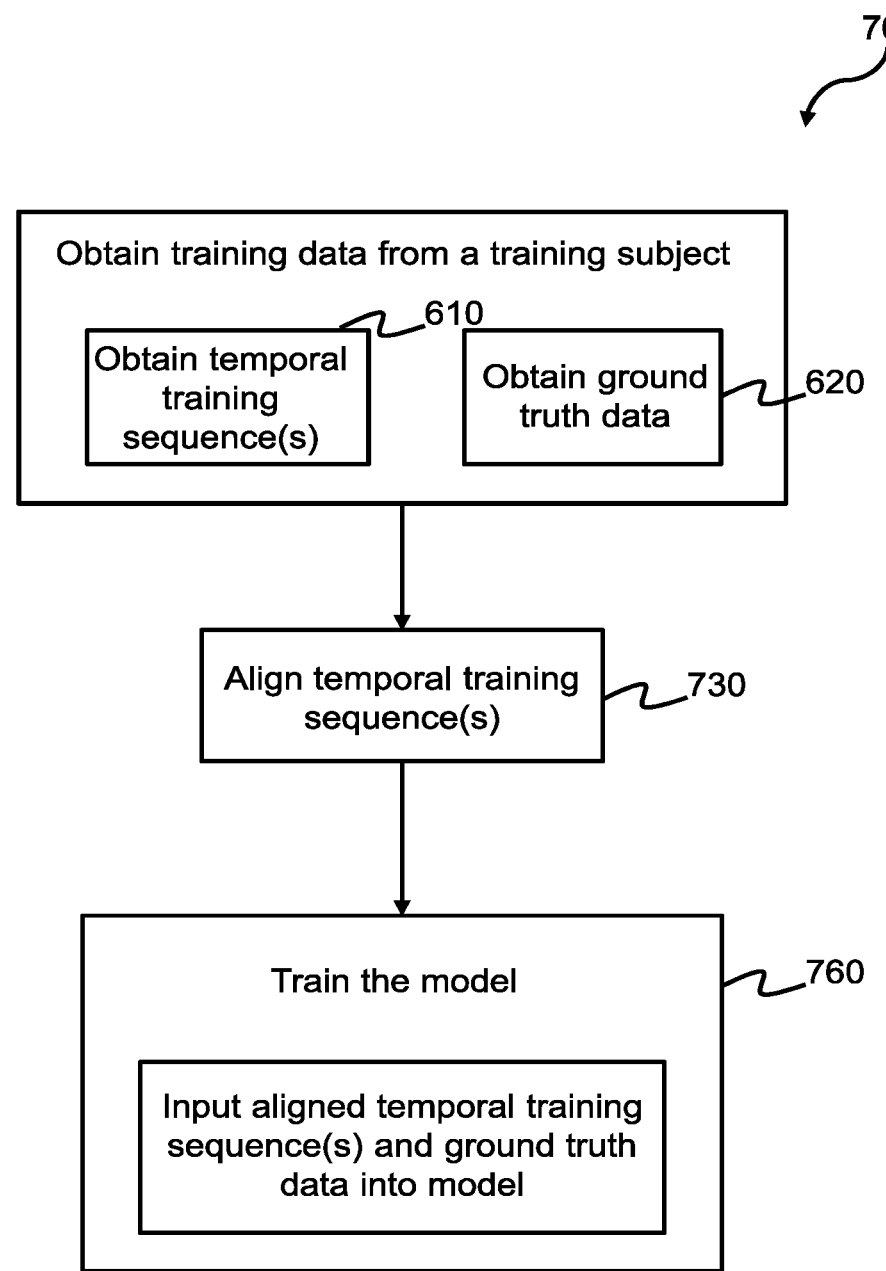
FIG. 6B is a flowchart illustrating a method of training a model for assessing the area of interest in the circulatory systems of subjects, in which the method further comprises aligning temporal training sequences.

FIG. 6B illustrates another computer implemented method 700 for training a model. The method 700 is used to train models suitable for use in the method of FIG. 2B. Step 610 is the same as in the method 600 of FIG. 6A. In this step, the processor 544 obtains temporal training sequences from the ultrasound system 510. Step 620 is also the same as in the method 600. In this step, the processor 544 obtains ground truth data corresponding to the temporal training sequences obtained in step 610.

The method 700 of this example differs from the method 600 in that models of a different type are trained. These are the models used in the inference method 300 of FIG. 2B. As explained previously above each of the models comprises a spatio-temporal fully convolutional neural network. These models are designed to accept, as input, temporal sequences that have been aligned (whereby each temporal sequence has a predetermined uniform length, and each temporal sequence starts and finishes at a defined point of the heartbeat). To train these models, it is first necessary to pre-process the temporal training sequences to produce aligned temporal training sequences. The alignment process is essentially the same as that of step 330, in FIG. 2B, described above—the processor 544 shifts, and decimates or interpolates, each of the temporal training sequences, to achieve the desired common alignment. Following this step, each temporal training sequence of frames may start and end at a predetermined point in the heartbeat, such as a P, Q, R, S, or T wave.

This substantially reduces the amount of variability in the training data. In turn, this may permit models to be trained using smaller quantities of training data, since the models do not need to learn to deal with such wide variability.

In step 760, the processor 544 trains each model, based on the aligned temporal training sequences produced in step 730 and the ground truth data obtained in step 620. The spatio-temporal fully convolutional neural networks used for the models in the method of FIGS. 2B and 6B are trained using end-to-end training. That is, the model learns to directly infer the output data (characterising the extent of calcification of the aortic valve) from the input data (that is, the temporal sequence of ultrasound image frames), without the need for intermediate steps, such as the separate feature extraction step performed by the CNN in the methods of FIGS. 2A and 7A. The trained models produced in step 760 are output for use in the method of FIG. 2B.

Note that, although the examples of FIGS. 2A and 6A, on the one hand, and FIGS. 2B and 6B, on the other hand, has been described as separate examples, it is possible that they may be combined. For instance, an inference method may be provided that is a hybrid of the methods 200 and 300. In such a hybrid method, some of the models may be based on spatiotemporal fully convolutional neural networks, while others may be based on the architecture of a CNN and RNN in series.

Note also that, in some cases, temporal sequences (and temporal training sequences) may already be available in aligned form. This can avoid the need for a pre-processing step 330, 730 to align each sequence, in the methods of FIGS. 2B and 6B. It may also help to reduce the amount of training data that is required to train the models to a given desired level of accuracy (for example, in the case described above with reference to FIGS. 2A and 6A). For example, the ultrasound systems 110 and 510 may automatically produce temporal sequences in aligned form, with a set number of image frames, starting at a predetermined trigger point in the heartbeat, such as a P-wave.

Figure 6C:
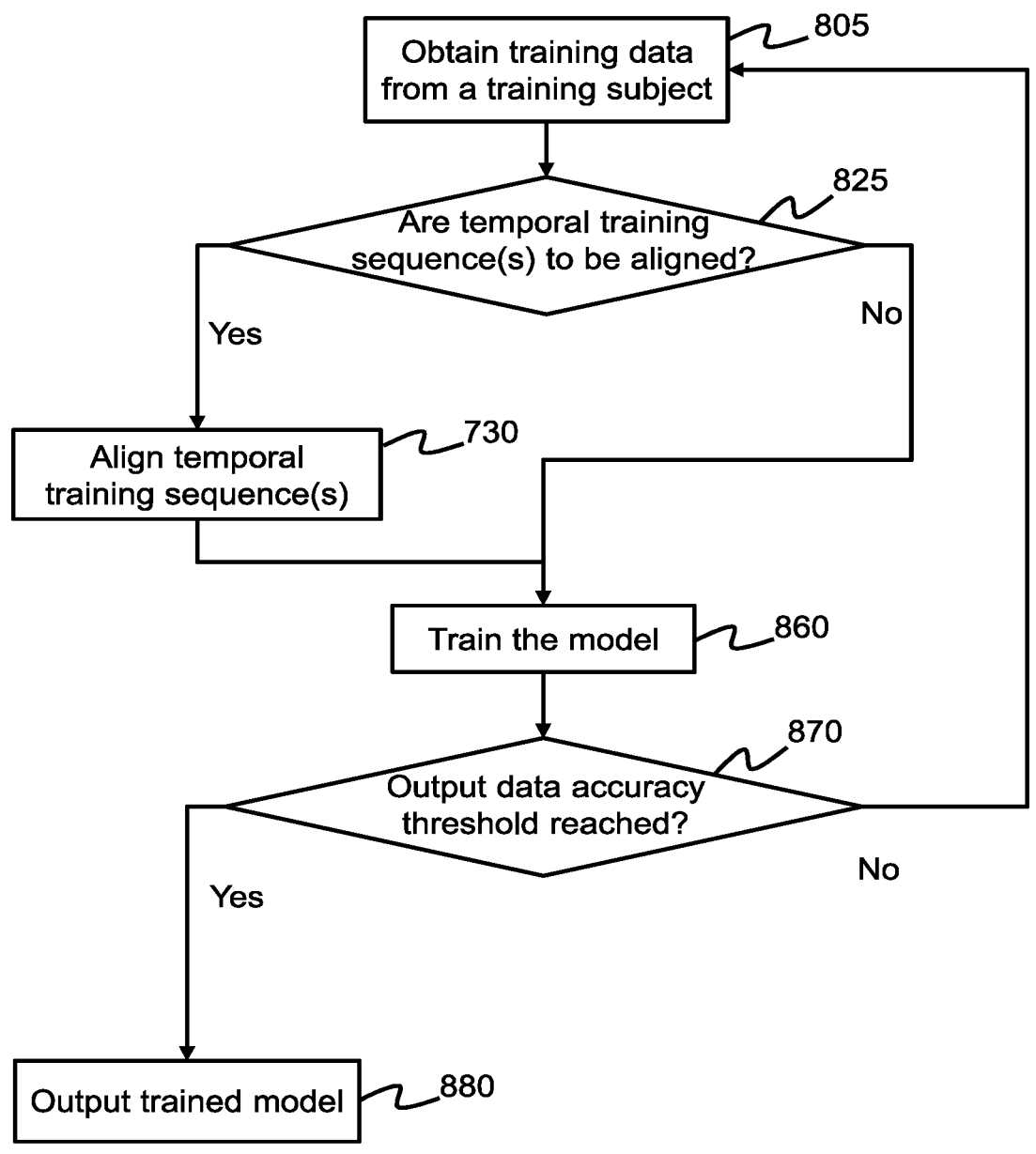
FIG. 6C is a decision tree showing the decisions made in the method of training the model before a trained model is produced.

FIG. 6C is a decision flow tree illustrating in greater detail how the training process may be carried out incrementally, using temporal training sequences obtained from individual subjects. In step 805, the processor 544 obtains training data for a given training subject. The training data comprises one or more temporal training sequences from one or more echocardiograms of the subject, and at least one item of ground truth data, such as an actual assessed AVC score for that subject (which may be obtained based on CT scan data, separately from the echocardiogram).

In step 825, the processor checks whether the temporal training sequences require alignment. This would be the case if the training sequences are provided in unaligned form (with arbitrary lengths, durations, and start and finish points), and the model to be trained requires temporal sequences of fixed length, starting and finishing at predetermined points of the heartbeat. If alignment is required, the method proceeds to step 730, in which the one or more temporal training sequences are aligned. If alignment is not required (either because the model does not require it, or because the temporal training sequences are already lined), then the method proceeds directly to step 860, for training of the model. Step 860 may comprise one iteration of the backpropagation algorithm for each of the one or more temporal training sequences.

After step 860, the method proceeds to step 870. Here, the processor 544 checks whether the output data produced by the model in its current state of training is sufficiently accurate. If so, the computer 540 outputs the trained model (step 880). If not, a further iteration of the training is required. The method returns to step 805, where the processor obtains training data for another training subject and repeats the incremental training process for this new training data. The method proceeds in this way, iterating over the training data of different training subjects, until the desired level of accuracy of the output data is achieved.

Methods and systems according to some examples of the present disclosure may use a trained model to predict an AVC score, such as an Agatston score, from echocardiogram data. The model may be trained using ground truth data generated by obtaining a CT scan of the training subject. The ground truth Agatston score may be derived from the CT scan data. In this way, the model can be trained to produce output data predicting the Agatston score for any given subject, without that subject needing to undergo a CT scan. This can make methods and systems according to the present disclosure more suitable for regularly monitoring the condition of a subject over time. Regular echocardiograms may pose a lower risk than regular CT scans, because a CT scan involves irradiating the subject with X-rays.

It should be noted that the above-mentioned embodiments illustrate rather than limit the invention, and that those skilled in the art will be able to design many alternative embodiments without departing from the scope of the appended claims.

The ultrasound image frames may be three-dimensional, whereby the temporal sequence of ultrasound image frames represents the area of interest in three spatial dimensions and one temporal dimension.

In an example not according to claim 1, the area of interest in the circulatory system need not be the aortic valve. It could be any area within the circulatory system. In some examples outside the scope of claim 1, the area of interest may be the mitral valve of the heart. The condition of the mitral valve may be assessed to determine whether (and to what extent) mitral valve regurgitation is occurring. A method according to such an example may be useful in planning a mitral clip procedure or a transcatheter mitral valve replacement (TMVR) procedure.

The temporal sequences (and temporal training sequences) may be obtained from ultrasound systems imaging an area of interest in the circulatory system outside of the heart. Likewise, the condition of the area of interest may be determined based on a metric other than the extent of calcification of the area of interest.

In some embodiments, the temporal sequence and the one or more temporal training sequences may be defined by a fixed duration. This fixed duration may be determined by measuring the duration of the periodic event using an ECG, if the periodic event is the heartbeat of the subject. The temporal sequence and one or more temporal training sequences may have a duration that is a fixed proportion of the period of the periodic event. For example, each sequence may have a duration that is 1.2 times the period of the respective periodic event. Alternatively, each sequence may have a duration that is exactly one period of the respective periodic event. In one instance, the duration of the temporal sequence (or temporal training sequence) may span from a P wave to the next P wave.

In the examples described above, it was assumed that the temporal sequences obtained from the echocardiograms had a fixed, uniform frame rate (at least prior to any temporal scaling involved in the aligning process). In other examples, different frame rates may be used for different sequences.

If a temporal sequence comprises 3D ultrasound image frames, then a 3D volumetric segmentation may be performed using 3D U-Net. Of course, segmentations may also be performed by trained models other than U-Net or 3D U-Net. In some embodiments, a segmentation may be generated from a saliency map via thresholding, to indicate at least one region of the area of interest. The saliency map may be generated using a guided backpropagation algorithm. Alternatively, the saliency map may be generated via any other suitable algorithm, such as a guided CAM backpropagation algorithm. In some embodiments, the segmentation may be spatial—operating on the image frames individually; in some embodiments, the segmentation may be spatiotemporal, operating on sequences of image frames collectively.

As explained above, the AVC score may be a predicted Agatston score, which is a known metric for determining the extent of calcification of the aortic valve. The Agatston score (which may comprise a numerical score) reflects the total area of calcified deposits seen in the temporal sequence and the density of those deposits. An Agatston score of 0 suggests there are no calcium deposits detected in the temporal sequence and, as such, the subject is unlikely to suffer from heart disease. More specifically, for the example given above, the subject is unlikely to suffer from aortic valve stenosis or require a TAVR procedure. A higher Agatston score suggests that calcium deposits detected in the temporal sequence pose some risk to the subject. An Agatston score greater than about 1200 or 1300 (for a woman), or greater than about 2000 (for a man) may suggest that the subject has severe aortic stenosis. This would imply an elevated risk of developing heart disease as a result of the calcium deposits, and that a TAVR procedure is likely to be required. It should be understood that other thresholds may be used instead of or in addition to the thresholds mentioned above. Further information about AVC grading may be found, for example, in Simard et al. ("Sex-Related Discordance Between Aortic Valve Calcification and Hemodynamic Severity of Aortic Stenosis", Circulation Research. 2017; 120:681-691) and Clavel et al. ("The Complex Nature of Discordant Severe Calcified Aortic Valve Disease Grading", JACC Vol. 62, No. 24, 2013:2329-38).

The example illustrated in FIG. 4A, in which one temporal sequence is input into three trained models, and each trained model outputs one item of output data, is a non-limiting example. In other examples, a single trained model may produce more than one item of output data. In some examples, a single trained model may produce all of the required output data. For example, a single trained model could be trained to produce both an AVC score and a predicted likelihood of a paravalvular leak.

Demographics of the subject, other than the sex of the subject, may be taken into consideration in order to obtain an accurate risk level for the subject, by applying different thresholds for each demographic. For example, there may be different threshold values for subjects in different body mass index categories, for subjects with different physical activity levels, for subjects with different diets, or for subjects with different smoking statuses. For example, if two subjects differ only in smoking status, the subject with the more extensive smoking history may be at greater risk of heart disease, and so may have a lower threshold value for determining their risk level than the subject with the smaller smoking history.

Instead of solely relying on applying different thresholds for different demographics of subjects, the method 200 could include training the one or more models for specific demographics of subjects. As an example, the subjects may be split into a first set of subjects and a second, different set of subjects. This split into different sets of subjects could be based on sex, age group, body mass index category (for example healthy, overweight, obese), physical activity level, diet, or smoking status. One or more first models may be trained to produce output data for the first set of subjects and one or more second models may be trained to produce output data for the second set of subjects. The subjects may be split into a greater number of sets of subjects. One or more third models may be trained to produce output data for a third set of subjects.

In some embodiments, a model may be trained via end-to-end learning. In other embodiments, a separate step of feature extraction may be introduced. In this extra step, the dimensionality of the input data (the temporal training sequence or temporal sequence) is reduced before it is input into a second, separate model for classification or other inference.

The memory 146, 546 may store one or more computer programs (or software or code) and/or data. The computer programs may include an operating system for the processor 144, 544 to execute in order for the computer 140, 540 to function. The computer programs stored in the memory 146, 546 may include computer programs according to embodiments of the invention or computer programs that, when executed by the processor 144, 544, cause the processor 144, 544 to carry out a method according to an embodiment of the invention. These computer programs may be stored on another computer readable storage medium, instead of, or in addition to, their storage in the memory 146, 546.

The processor 144, 544 may be any data processing unit suitable for executing one or more computer readable program instructions, such as those belonging to computer programs stored in the memory 146, 546. As part of the execution of one or more computer-readable program instructions, the processor 144, 544 may store data to and/or read data from the computer-readable storage medium and/or the memory 146, 546. The processor 144, 544 may comprise a single data processing unit or multiple data processing units operating in parallel or in cooperation with each other. The processor 144, 544 may, as part of the execution of one or more computer readable program instructions, store data to and/or read data from the computer-readable storage medium and/or the memory 146, 546.

The invention claimed is:

1. A computer-implemented method comprising:
obtaining a temporal sequence of ultrasound image frames of an aortic valve of a subject, wherein the temporal sequence of the ultrasound image frames comprises a duration greater than or equal to a heartbeat;
obtaining a spatio-temporal fully convolutional neural network configured to determine:
calcification of the aortic valve within the ultrasound image frames; and
motion associated with the aortic valve between the ultrasound image frames;
inputting the temporal sequence of the ultrasound image frames into the spatio-temporal fully convolutional neural network;
generating, as an output of the spatio-temporal fully convolutional neural network, an aortic valve calcification (AVC) score defining a severity of the calcification of the aortic valve of the subject; and
providing, on a display, a graphical user interface (GUI) comprising the temporal sequence of the ultrasound image frames and an output based on the AVC score,
wherein the spatio-temporal fully convolutional neural network is trained by iteratively comparing:
ground truth data comprising numerical scores defining the severity of calcification of the aortic valve of a plurality of training subjects; and
the AVC scores for the plurality of training subjects that are generated based on a plurality of temporal training sequences of the ultrasound image frames of the aortic valve of the plurality of training subjects.

2. The method of claim 1, wherein each of the ultrasound image frames in the temporal sequence is three-dimensional.

3. The method of claim 1, wherein the temporal sequence starts at a same predetermined point of the heartbeat.

4. The method of claim 1, wherein the temporal sequence has a predetermined number of the ultrasound image frames.

5. The method of claim 1, wherein the temporal sequence has a duration that is a fixed proportion of the heartbeat.

6. The method of claim 1,
wherein the spatio-temporal fully convolutional neural network is trained using a first set of training subjects, and a second spatio-temporal fully convolutional neural network is using a second set of subjects comprising a different demographic than the first set of training subjects.

7. A non-transitory computer readable medium comprising computer program code configured to cause a processor to carry out the method of claim 1 when the computer program code is executed by the processor.

8. The method of claim 1, wherein the AVC score comprises a predicted Agatston score such that the AVC score does not require a computed tomography (CT) scan.

9. The method of claim 1, wherein the numerical values comprise Agatston scores generated using computed tomography (CT) scans.

* * * * *